United States Patent [19]

Kedem

[11] Patent Number: 5,205,828
[45] Date of Patent: Apr. 27, 1993

[54] EPIDURAL NEEDLE LOCATION INDICATOR ASSEMBLY

[76] Inventor: Dan Kedem, 43 Weizmann Street, 76283 Rehovot, Israel

[21] Appl. No.: 782,205

[22] Filed: Oct. 24, 1991

[51] Int. Cl.$^5$ .............................................. A61M 5/18
[52] U.S. Cl. .................................... 604/158; 604/165
[58] Field of Search ............... 604/274, 167, 157, 158, 604/134, 135, 136, 165

[56] References Cited

U.S. PATENT DOCUMENTS

| | | | |
|---|---|---|---|
| 1,527,291 | 2/1925 | Zorraquin | 604/158 |
| 3,792,703 | 2/1974 | Moorehead | 604/158 |
| 3,840,008 | 10/1974 | Noiles | 604/158 |
| 4,316,463 | 2/1982 | Schmitz et al. | 604/157 |
| 4,601,710 | 7/1986 | Moll | 604/274 |
| 4,747,414 | 5/1988 | Brussel | 604/157 |
| 4,793,363 | 12/1988 | Ausherman et al. | 604/165 |
| 4,966,585 | 10/1990 | Gangemi | 604/135 |
| 4,973,312 | 11/1990 | Andrew | 604/165 |
| 4,973,313 | 11/1990 | Katsaros et al. | 604/165 |
| 5,104,382 | 4/1992 | Brinkerhoff et al. | 604/165 |

OTHER PUBLICATIONS

Lumbar and Thoracic Epidural Anaesthesia by E. N. Armitage in Principles of Regional Anesthesia, pp. 81–91, edited by J. A. W. Wildsmith.

*Primary Examiner*—Paul J. Hirsch
*Attorney, Agent, or Firm*—Mark M. Friedman; Benjamin J. Barish

[57] ABSTRACT

An epidural needle location indicator device for semi-automatically indicating when an epidural needle has entered into the epidural space in preparation of the delivery of epidural anesthesia. The device can be used with conjunction with a conventional Tuohy needle and takes advantage on the reduction in pressure experienced upon entry into the epidural space causes a visible controlled forward movement of the stilette.

13 Claims, 5 Drawing Sheets

EPIDURAL NEEDLE LOCATION INDICATOR ASSEMBLY

FIELD AND BACKGROUND OF THE INVENTION

The present invention is of an epidural needle guide device and, more particularly, of a modification in currently known epidural injection systems which allows the anesthetist to properly locate the needle tip in the epidural space more automatically with less reliance on the needle's feel via the operator's hands.

Epidural anaesthesia is well-established as a substitute for, or an adjacent to, general anesthesia for operative surgery. Epidural block at the lumbar and lower thoracic level is suitable for most gynecological and urological work, for some general abdominal and orthopedic surgery.

To administer epidural anesthesia the anesthetist must first locate a needle in the epidural space. A number of techniques for guiding the needle tip into the epidural space are in current use. All techniques are based on the difference in resistance offered by the various tissues through which the needle passes.

Perhaps, the most widely used needle in epidural anesthesia is the Tuohy needle, which has a shaft which is usually 8 cm long. The needle wall is thin so that the lumen will admit a catheter of reasonable size. A stilette prevents coring of superficial tissues and increases rigidity so that the needle does not bend when re-directed. The point is relatively blunt and is contoured so that a catheter emerges at an angle of about 20 degrees. The needle may be equipped with a winged hub which may provide better control.

Proper placement of the needle tip is generally determined by the feel of the needle as it travels through the tissues on its way to the epidural space. The needle first pierces the skin, then travels through superficial tissues, then through the supraspinous ligament, the interspinous ligament, the ligamentum flavum, and finally into the epidural space.

To test the location of the needle, one could, for example, do the following. With the needle inserted perhaps 2 cm into the patient's back, it is useful to test its 'feel' in the tissues by moving the hub of the needle up and down. Since the tip is able to move relatively freely in the superficial tissues, the needle moves like a see-saw, the fulcrum being its point of entry at the skin. When the needle is advanced further, the tip eventually engages in the ligamentum flavum and if the hub is again moved up and down, the 'feel' is very different since the needle is now fixed at two points along its length and behaves like a springboard with restricted motion.

Because of their different densities, the intervertebral ligaments offer varying degrees of resistance to both the advance of a needle and to the injection of liquid. Identification of the epidural space may depend on the fact that saline, being incompressible, cannot be injected if the needle tip is in the ligament. Once the epidural space is entered, both the advance of the needle and the injection of saline become easier since the space contains only loose tissue.

The whole needle-syringe assembly is advanced slowly while steady pressure is applied to the plunger with the thumb. Entry to the epidural space is marked by the sudden ability to inject saline, 5 ml of which is usually sufficient to establish that the needle is correctly placed. The technique suffers from the disadvantage of being entirely dependent on the feel of the anesthetist. An error in judgment on the part of the anesthetist can lead to the penetration of the dura and lead to serious and undesirable medical complications for the patient.

Traditionally it has been believed that there is a subatmospheric pressure within the epidural space due to transmission of the intrapleural pressure through the intervertebral foramina. It has also been suggested that the pressure is due simply to 'tenting' of the dura by the point of the needle. Whichever is the case, air or liquid will tend to be sucked in through the needle when its tip enters the epidural space.

Two techniques have been described to take advantage of the under-pressure. In the hanging drop method (Soresi, Peridural Anesthesia: A Preliminary Report, Medical Record (New York) 35: 165-166 (1932)), a drop of fluid is applied to the hub of the needle once its tip is embedded in the ligaments. As the tip enters the space, the drop of fluid is sucked in.

In the balloon method (Macintosh, New Inventions 2: Extradural Space Indicator, Anaesthesia 5: 98 (1950)), a small balloon is attached to the needle and is inflated through a side port. As the needle tip enters the space the balloon deflates.

Both of these techniques suffer from the disadvantage of being complicated and less than reliable.

There is thus a widely recognized need for a method of guiding the needle tip of an epidural anesthetic needle into the epidural space which does not depend heavily on the feel and judgment of the anesthetist.

It would be desirable to have a method of guiding the needle to its proper place quickly and efficiently and semiautomatically without fear of falling short of the epidural space or of overshooting it and penetrating tissues lying beyond the epidural space.

SUMMARY OF THE INVENTION

According to the present invention there is provided an epidural needle location indicator assembly capable of indicating when a needle traveling through hard tissue first penetrates soft tissue, comprising: (a) a housing; (b) a hollow needle secured near its posterior end to the anterior end of the housing and having an anterior end which is directed laterally; (c) a displaceable piston located in the housing, capable of traveling between a fixed forward displaceable piston position and a fixed back displaceable piston position, the piston positions being a pre-selected distance apart; (d) a flexible blind end catheter located in the needle, passing through the displaceable piston, the blind end catheter preventing coring of tissues during the forward travel of the needle and serving to transmit tissue pressure to the displaceable piston; (e) a grasping means connected to the displaceable piston for alternately grasping or releasing the catheter; (f) means for releasably locking the displaceable piston to the housing at the back displaceable piston position; and (g) means for biasing the displaceable piston toward the front piston position.

According to further features in preferred embodiments of the invention described below the needle is a Tuohy needle, and the insert is a stilette.

According to still further features in the described preferred embodiments, the locking means is a safety latch, preferably of a bayonet type, and the means for biasing the displaceable piston includes the use of a compressible fluid, or, preferably a spring, more preferably a coil spring, connected to a biasing piston located posterior to the displaceable piston.

According to another embodiment of the present invention both the displaceable and the biasing pistons contain apertures capable of accommodating a stilette, or, preferably, a catheter, more preferably a blind end catheter. This embodiment includes means connected to the displaceable piston capable of alternately grasping or releasing the catheter. Preferably, the displaceable piston also includes an elliptic lock catch. Throughout the discussion which follows the terms "anterior" or "forward" refer to the portion of the described item closer to the spinal cord of the patient while the terms "posterior" or "back" refer to the position of the described item farther away from the patient's spinal cord.

The present invention successfully addresses the shortcomings of the presently known epidural needle location indicator configurations by providing a device which facilitates the proper placement of the tip of the epidural needle in the epidural space in a manner which is largely automatic and which relies to a much lesser extent on the discretion and judgment of the anesthetist. It should be noted that use of the device according to the present invention is not limited to use in epidural anesthesia. Rather, the device according to the present invention may be used whenever it is desired to know, during the insertion of a needle through a series of tissues, when the needle leaves relatively hard tissue and starts to penetrate relatively soft. For illustrative purposes only, the device of the present invention is described below with reference to its application in epidural anesthesia.

The present invention discloses a novel device, which is a modification of the widely used Tuohy needle configuration. To facilitate the explication of the device according to the present invention it is necessary to briefly review the mode of operation of the presently known Tuohy needle. Tuohy needles are prepared by the manufacturer by inserting a stilette into the needle so that the stilette is flush with or extends somewhat beyond the anterior end of the needle. The anterior end of the stilette, and in some cases also the anterior tip of the needle, is then cut at the desired angle, leaving the stilette tip flush with the tip of the needle.

The device according to one embodiment of the present invention is sold ready to use as a kit with the stilette already inserted. The anesthetist pushes the needle into the patient's back, constantly monitoring the location of the needle tip by the resistance he feels to the movement of the needle. The presence of the stilette prevents tissue from entering the needle through the process of coring. Typically, the anesthetist pushes the needle until he senses the increased resistance offered by the ligamentum flavum. The anesthetist then connects a low-resistance syringe and continues to push the needle forward. Upon the entry of the needle tip into the epidural space, a noticeable drop in resistance is experienced which is visible through the loss of fluid from the syringe and through the needle. At this point the anesthetist discontinues the forward progress of the needle, immobilizes the needle, pulls out the stilette and replaces it with a catheter which is then used for the injection of the anesthetizing fluid. Alternatively, the anesthetist can proceed to inject anesthetizing fluids through the empty needle without using a catheter.

A difficulty with the present method is that locating the needle tip properly depends to a large extent on the sensitivity and judgment of the anesthetist. This difficulty is largely eliminated when using an epidural needle guide device according to the present invention.

According to one embodiment of the present invention, the stilette is connected at its posterior end to a displaceable piston located in the syringe. The piston, which is constrained to move between two fixed points of pre-selected separation, is immobilized in its posterior position by a latch. Means are provided for biasing the piston anteriorly. In one embodiment this is accomplished by connecting the anterior piston to a biasing piston by a spring. The biasing piston can be set in one of two positions. The posterior position does not compress the spring. The anterior positions tenses the spring, anteriorly biasing the displaceable piston.

The device according to the present invention may be sold with the biasing piston in the posterior position. Just prior to use, the biasing piston is set in its anterior position, biasing the displaceable piston anteriorly. The needle is then inserted in the patient's back. When the anesthetist senses, by the increased resistance, that the needle tip has entered the ligamentum flavum, the anesthetist releases the displaceable piston by simply unlatching the lock so that the displaceable piston is free to move anteriorly. The displaceable piston will not move since the spring force is such that it is unable to overcome the resistance produced by the ligamentum flavum, yet can easily overcome the resistance of the epidural space.

The anesthetist, having released the displaceable piston, continues to push the needle forward, without the need to pull out the stilette and replace it with a syringe as in present techniques. As soon as the needle tip enters the epidural space the resistance drops. The pressure drop is sensed by the anterior end of the stilette. The pressure drop is sufficient to allow the spring to push the displaceable piston, and the attached stilette, forward a fixed distance. Having observed the forward movement of the displaceable piston, the anesthetist discontinues the forward progress of the needle. He may now immobilize the needle, withdraw the stilette and replace it, if desired, with a catheter, as before.

In another, and preferred, embodiment of the present invention, a stilette is not used at all. Rather, the needle comes equipped with a catheter, preferably a blind end catheter, which runs from the tip of the needle, through both the displaceable and biasing pistons and out the posterior end of the syringe. The needle is inserted as before. However, when the epidural space is reached, the displaceable piston jumps forward, passing the anterior tip of the catheter into the epidural space tissue and thereby exposing the openings near the tip of the catheter and making them immediately available for the injection of anesthetizing fluids.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a needle assembly, typically an epidural needle assembly, which can aid in guiding the anesthetist in bringing the needle tip to its proper location in the epidural space semi-automatically with reduced reliance on the feel of the needle in the hand of the anesthetist. The present invention can be better understood with reference to the enclosed illustrative figures.

Figure 1:
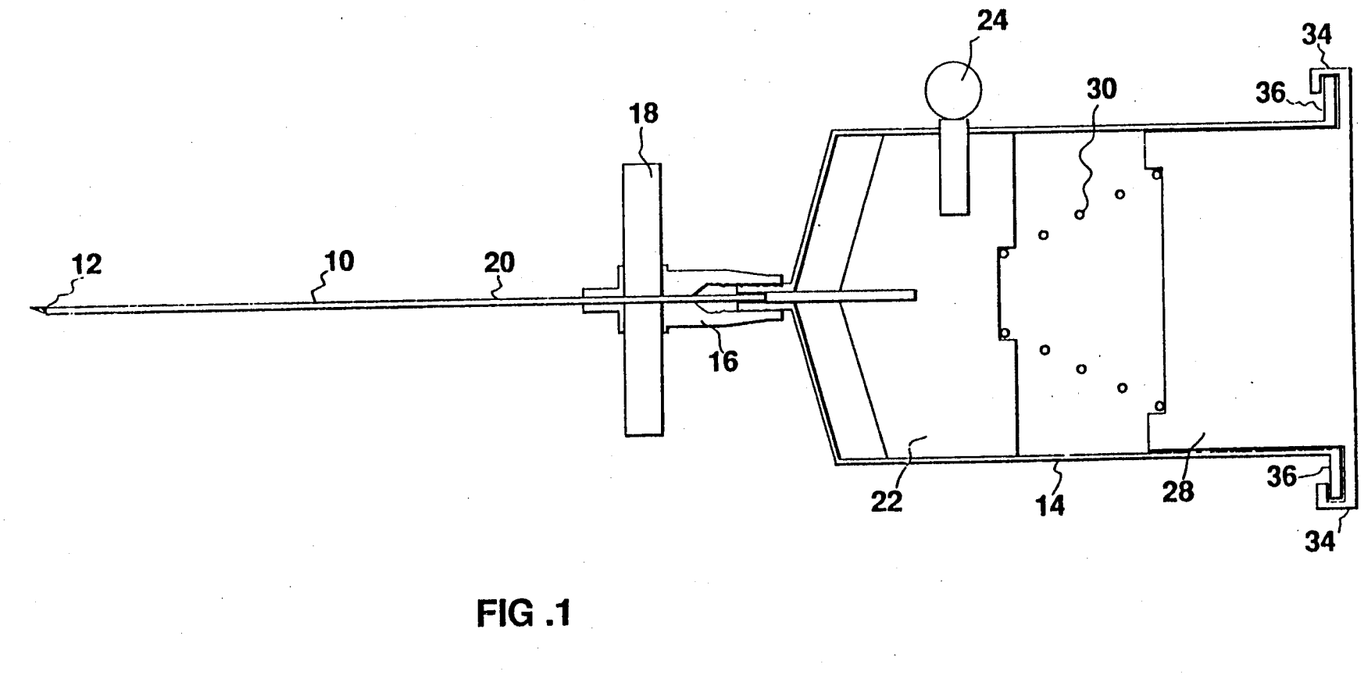
FIG. 1 is a cross-sectional view of a device according to the present invention having a pin safety latch and a winged hub.

Referring now to the figures, FIG. 1 illustrates one possible configuration of the device according to the present configuration. The device includes a needle 10. Any of a number of epidural needle types can be used in conjunction with the device of the present invention. For illustrative purposes, a Tuohy needle, which is very popular in epidural applications, is shown in the figures and in the discussion below. A Tuohy needle is characterized in that its tip 12 is cut off at an angle to the axis of the needle. The oblique angle facilitates the injection of anesthetizing material once tip 12, which penetrates the patient in a direction perpendicular to the spinal cord, enters the epidural space which runs parallel to the spinal cord.

Needle 10 is attached to a housing or case, typically a syringe 14 through a hub 16. Hub 16 may be of any convenient type, such as the Luer or Luer Lock types. Hub 16 may optionally include a wing 18 which may be useful in guiding the device into the patient and in immobilizing the device when the stilette is withdrawn and when the catheter is inserted. Wing 18 is omitted in FIG. 2.

Needle 10 contains a stilette 20, typically a fitted plastic rod which fills interior of needle 10 but which is also capable of being extracted from needle 10. Stilette 20 runs the entire length of needle 10 from its tip 12 and through its posterior end. Stilette 20 extends beyond the posterior end of needle 10 and is attached to displaceable piston 22. Displaceable piston 22 is of a size and shape so as to be capable of sliding within syringe 14 between a fixed posterior and a fixed anterior position located a predetermined distance apart, except that displaceable piston 22 is capable of being releasably locked and immobilized by a constraining means at its posterior position.

Figure 2:
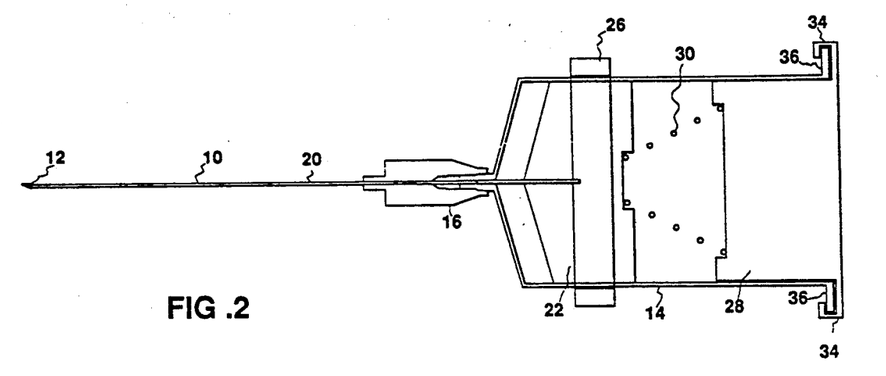
FIG. 2 is a cross-sectional view of a device as in FIG. 1 but having a bayonet safety latch and having no winged hub.

Any suitable locking means may be used. Shown in FIG. 1 is a pin 24 which penetrates the syringe 14 from the outside and engages displaceable piston 22 thereby immobilizing it. Pin 24 is removed by the anesthetist at the proper time, thereby releasing displaceable piston 22 and allowing to move within syringe 14. Another constraining means is shown in FIG. 2. Instead of pin 24, used in FIG. 1, FIG. 2 uses a bayonet safety latch 26 which can be deployed by the anesthetist to release displaceable piston 22.

Figure 3:
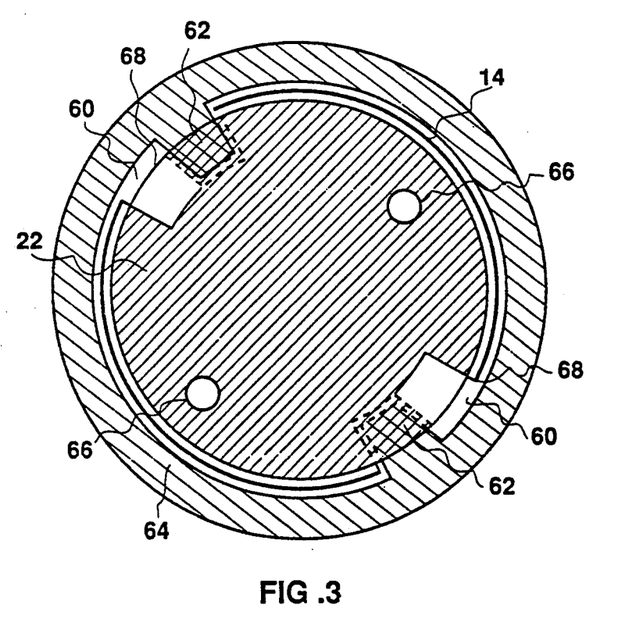
FIG. 3 is a cross-sectional view of a bayonet safety latch of FIG. 2 showing its workings.

The operation of bayonet safety latch 26 can be better understood with reference to a typical example of such a latch as shown in FIG. 3, which shows bayonet safety latch 26 as viewed looking posteriorly from the anterior end of housing 14. Housing 14 features two slits 60 cut at its sides which run perpendicular to the housing axis. Slits 60 are sufficiently wide so as to accommodate a pair of bayonet teeth 62 and sufficiently long so as to accommodate the movement of bayonet teeth 62 between the locked and unlocked positions. Bayonet teeth 62 are mountable onto a bayonet ring 64 whose inner diameter is slightly larger than the outer diameter of housing 14.

Displaceable piston 22 features a pair of tracks 68 which run parallel to the axis of housing 14 for a sufficiently long distance as to accommodate the full travel distance of displaceable piston 22 between its back and its forward positions, and which are sufficiently wide as to accommodate bayonet teeth 62. Displaceable piston 22 may also feature air holes 66 to allow air to escape during forward movement of displaceable piston 22 so as to avoid trapping air pockets which could result in air compression and in the inhibition of the forward motion of displaceable piston 22.

To install bayonet safety latch 26 one manipulates displaceable piston 22 into its posterior-most position. One then fits bayonet ring 64 over housing 14 so that bayonet ring 4 is located opposite slits 60. Bayonet teeth 62 are then pressed through bayonet ring 64 so as to be firmly mounted onto bayonet ring 64 and to engage displaceable piston 22 so as to keep it from moving anteriorly. It is in this condition that the device is presented to the anesthetist.

In use, when the anesthetist determines that the needle tip has entered the ligamentum flavum, he releases displaceable piston 22 by grasping bayonet ring 64 and rotating it slightly so that bayonet teeth 62 no longer engage displaceable piston 22 but rather enter slots 68 which allows displaceable piston 22 to move anteriorly once the tissue pressure is sufficiently reduced so that the force exerted by the biasing means is able to overcome the tissue pressure.

Displaceable piston 22 may be anteriorly biased by any convenient means. For example, housing 14 could contain a compressible fluid in the space anterior to biasing piston 28 which, when properly compressed, could be used to urge displaceable piston 22 forward. The fluid may be hydraulic liquid, such as oil, or it may be a gas, such as nitrogen.

An alternative, and preferred, method of biasing displaceable piston 22 is by means of a spring or similar mechanical device. In one embodiment, illustrated in the figures, a loadable spring is included. Mounted near the posterior end of syringe 14 is a biasing piston 28. Biasing piston 28 is connected to displaceable piston 22 by any means capable of translating a change in position of biasing piston 28 into an anteriorly-directed biasing force on displaceable piston 22. Preferably, displaceable piston 22 and biasing piston 28 are connected by a spring 30.

Spring 30 may be a cylindrical spring (not shown) or it may be a spring coil featuring a spiral configuration which is capable of compressing without adjoining coils touching each other, which configuration can lead to space savings, should that be desired.

Figure 4:
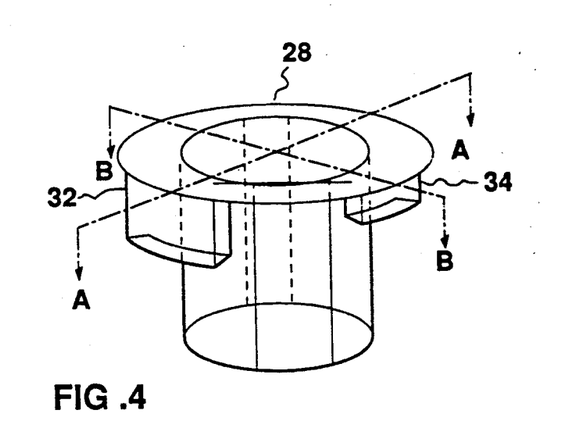
FIG. 4 is a perspective view of the posterior end of the biasing piston showing the two types of catches to allow the biasing piston to be located at one of two different positions.
Figure 5:
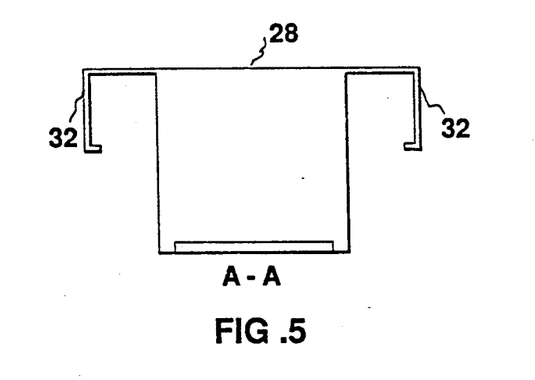
FIG. 5 is a cross sectional view along cut A—A of the biasing piston of FIG. 4 showing the long catches for the loaded position.
Figure 6:
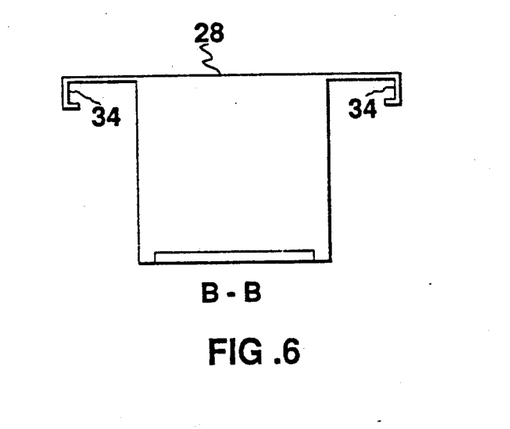

The structure of biasing piston 28 may be better appreciated with reference to FIG. 4, 5, and 6. The position of biasing piston 28 must be capable of being set at one of two pre-determined positions—the posterior setting and the anterior setting. One exemplary way of achieving this is to provide the posterior end of biasing piston 28 with two pairs of opposing catches. The long catches 32 and short catches 34 are capable of engaging a pair of opposing lips 36 (see FIG. 1, 2 and 7) located at the posterior end of syringe 14.

The principles of a device according to the present invention may be better understood with reference to the method of its operation, which is described next.

The anesthetist receives the device kit as shown in FIGS. 1 or 2, with displaceable piston 22 immobilized by pin 24 or bayonet safety latch 26, or by any other convenient means. Stilette 20 is already attached to displaceable piston 22 and extends the full length of needle 10.

The device is sold with biasing piston 28 in its posterior setting, with long catches 32 engaging lips 36. In this position biasing piston 28 is farthest from displaceable piston 22 so that little force is exerted on spring 30. This is in order to minimize or eliminate the deterioration of the properties of spring 30 during storage prior to use and to thereby increase the shelf-life of the device.

When the anesthetist is ready to use the device he must load spring 30. This is accomplished by pressing biasing piston 28 anteriorly sufficiently so as to disengage long catches 32 from lips 36 and to allow long catches 32 to clear lips 36, turning biasing piston 28 a quarter turn in either direction, and then releasing biasing piston 28 so as to allow short catches 34 to engage lips 36.

This manipulation of biasing piston 28 loads spring 30 thereby anteriorly biasing displaceable piston 22. As will be explained below, the force produced by spring 30 must be carefully preselected so that it will function properly during operation.

Once spring 30 has been loaded, the device is ready for use. Needle 10 is inserted into the patient in the usual way. At some point during the advance of needle 10 the anesthetist will feel a dramatically increased resistance to motion of needle 10, indicating that the ligamentum flavum has been reached. At this point the anesthetist will release displaceable piston 22 which has heretofore been immobilized by some convenient means, such as by pin 24 or bayonet safety latch 26.

Releasing pin 24 or bayonet safety latch 26 removes the artificial constraint on the motion of displaceable piston 22. Spring 30 is designed so that it is incapable of providing sufficient force to move displaceable piston 22 anteriorly when the needle tip 12 is in the high resistance ligamentum flavum tissue. Syringe 14 may be designed so that displaceable piston 22 is permanently prevented from moving posteriorly from its initial immobilized position.

With pin 24 or bayonet safety latch 26 released, displaceable piston 22 is thus free to move anteriorly provided the spring force can overcome the resistance to movement transmitted to displaceable piston 22 from the tissue via stilette 20. While needle tip 12 is traveling through the ligamentum flavum, displaceable piston 22 is prevented from displacing anteriorly by the resistance of the tissue and remains substantially in the position it had while immobilized.

Spring 30 is designed so as to provide sufficient force to move displaceable piston 22 anteriorly against the epidural space tissue pressure, which is considerably less than the tissue pressure encountered in the ligamentum flavum. As the anesthetist continues to push needle 10 forward there comes a point when the epidural space is penetrated by needle tip 12. As soon as the epidural space is penetrated, a relatively large pressure drop at tip 12 is experienced. Spring 30 immediately pushes displaceable piston 22, and thus stilette 0 which is attached to displaceable piston 22 anteriorly, causing the anterior tip of stilette 20 to protrude from the tip of needle 10 into the tissue. The forward progress of displaceable piston 22 and thus of stilette 20 is interrupted when displaceable piston 22 reaches its anterior position. The distance of travel between the immobilized posterior setting of displaceable piston 22 and its anterior-most position is carefully selected so as to place the anterior tip stilette 20 at a desirable location within the epidural space and so as to eliminate the risk that stilette 20 will puncture the far wall of the epidural space.

The abrupt motion of displaceable piston 22 alerts the anesthetist that the epidural space has been reached. The anesthetist can then stop the forward motion of needle 10, retrieve stilette 20 and insert a catheter (not shown) into needle 10 through which anesthetizing fluids may be introduced into the epidural space. Alternately, the anesthetist may retrieve stilette 20 and proceed to inject anesthetizing fluids directly through needle 10 without using a catheter.

Figure 7:
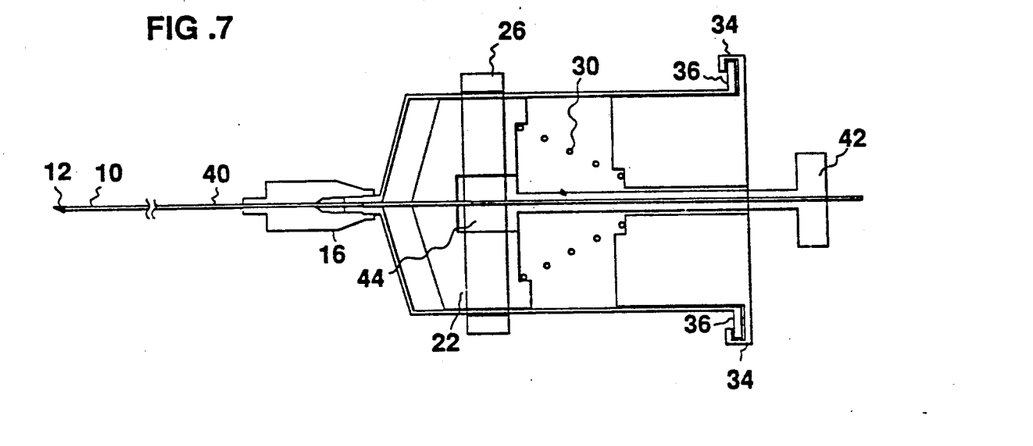
FIG. 7 is a cross-sectional view of an alternative embodiment which can be used with a blind end catheter.

An alternative embodiment of the device according to the present invention is illustrated in FIG. 7. The alternative embodiment features no stilette. Instead, the device comes equipped with a catheter 40. Catheter 40 is preferably of the blind end type featuring a closed anterior end with holes for ejection of fluids located radially at points near the close tip. The closed anterior end of catheter 40 prevents tissue from being cored into needle 10 during the forward progress of needle 10. In this way, catheter 40 is able to serve the function of a stilette during the insertion of needle 10 into the patient.

Figure 8:
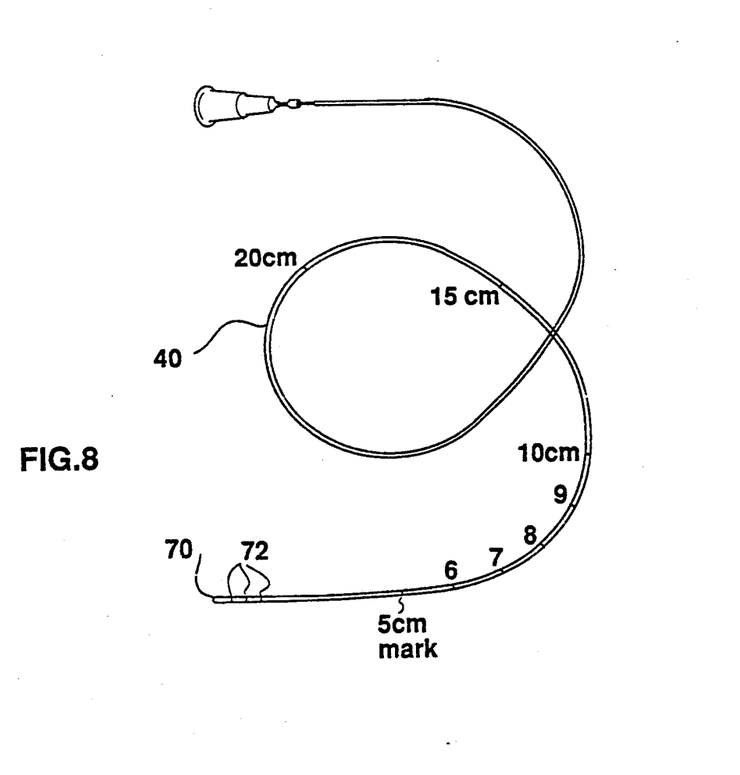
FIG. 8 is a view of an uninstalled blind end catheter of FIG. 7 showing the blind end and the openings for fluid passage.

Shown is FIG. 8 is a typical blind end catheter 40 of the type which can be used in conjunction with the present invention. Catheter 40 is closed at its tip 70 with fluids able to exit catheter 40 not through its tip 70, as would be the case in standard catheters, but rather through a series of holes 72 located near tip 70.

In contrast with stilette 20 of the previous embodiment which was connected at its posterior end to displaceable piston 22, catheter 40 passes through displaceable piston 22 as well as through biasing piston 28 and exits syringe 14 through its posterior end. Catheter 40 is housed in a guide 42 which is rigidly fixed to and is capable of sliding with displaceable piston 22. Guide 42 is slidably engaged to biasing piston 28 and extends posteriorly of biasing piston 28 so as not to prevent displaceable piston 22 from sliding forward until it contacts the anterior wall of syringe 14.

The anterior portion of guide 42 is a lock catch 44, which may be connected to, or which may be integral with displaceable piston 22, which is capable of alternately grasping and releasing catheter 40. Any convenient lock catch mechanism may be used. Two such mechanisms are illustrated in FIGS. 9–12.

Figure 9:
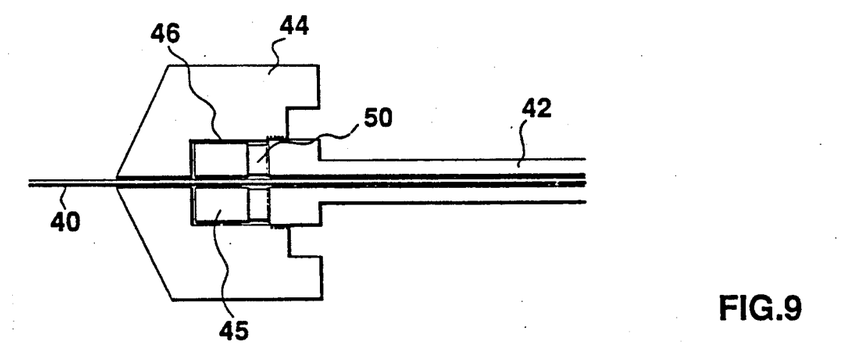
FIG. 9 is a cross-sectional view of a lock catch which can be used in conjunction with the embodiment depicted in FIG. 7.

FIG. 9 illustrates a conventional lock catch mechanism. Lock catch 44 contains a cavity 46, typically cylindrical in shape. Cavity 46 is partially filled with a rubber cylinder 48 which features a sufficiently large cylindrical hole through its center as to allow catheter 40 to freely move through rubber cylinder 48. Located immediately posteriorly from rubber cylinder 48 is a disc 50 made of a rigid material, typically metal. Disc 50 is rigidly mounted to guide 42 and has threads (not shown) which engage opposing threads (not shown) on the wall of cavity 46. Turning guide 42 in one direction tends to put pressure on rubber cylinder 46 causing it to put pressure on catheter 40 and thereby immobilizing it in place as a result of static friction forces.

Operation of such a device is be similar to the operation described above with reference to the basic embodiment, with several exceptions. Prior to use, catheter 40 is immobilized using the described lock catch 44. This may be done by the manufacturer or, alternatively, it may be done by the anesthetist just prior to use. Spring 30 is loaded as described above. Needle 10 is inserted into the patient as before. At the proper time, as described above, displaceable piston 22 is released. At some subsequent time displaceable piston 22, along with catheter 40 jump forward indicating that the epidural space had been reached, as above. Furthermore, the forward movement of catheter 40 serves to expose holes 72 near the catheter tip 70 thereby readying catheter 40 for injection of anesthetizing fluids.

At this point the anesthetist can immediately begin the injection of anesthetizing fluids through catheter 40, thereby saving the complications and delay involved in pulling out a stilette and inserting a catheter in its place.

Figure 10:
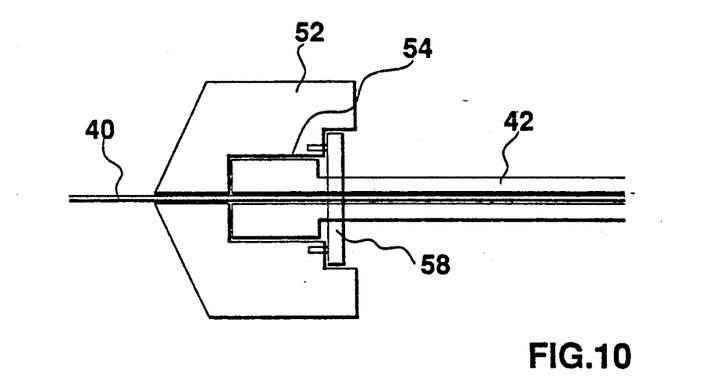
FIG. 10 is a cross-sectional view of an elliptic lock catch which can be used in conjunction with the embodiment depicted in FIG. 7.
Figure 11:
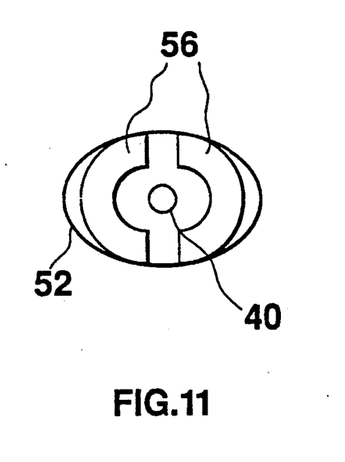
FIG. 11 is an end view of the catch of FIG. 10 showing the catch in the unlocked position.
Figure 12:
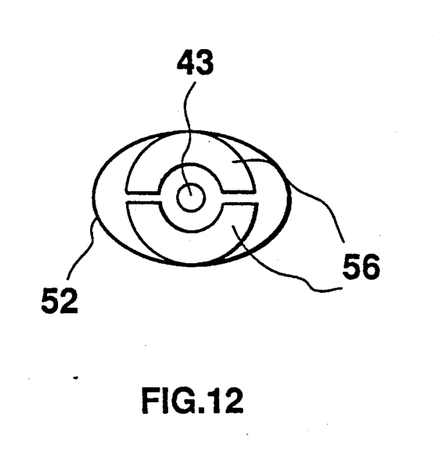
FIG. 12 is an end view of the catch of FIG. 10 showing the catch in the locked position.

Another lock catch mechanism, an elliptic lock catch 52, which, which may be connected to, or which may be integral with displaceable piston 22, is illustrated in FIGS. 10-12. Elliptic lock catch 52 features a cavity 54 which is elliptical, rather than circular, in shape. Located inside cavity 54 are two opposing annular members, typically cylinder halves 56, which surround catheter 40. Cylinder halves 56 are retained in place by locking disc 58 and are attached to guide 42.

In the position shown in FIG. 11 the cylinder halves 56 are widely separated and catheter 40 can freely move through lock catch 52. When guide 42 is turned a quarter turn in either direction cylinder halves 56 approach each other and squeeze catheter 40 thereby preventing it from moving. The operation of the epidural device is as described immediately above in the case of the conventional lock catch.

While the invention has been described with respect to two basic embodiment, it will be appreciated that many variations, modifications and other applications of the invention may be made.

What is claimed is:

1. An epidural needle location indicator assembly capable of indicating when a needle traveling through hard tissue first penetrates soft tissue, comprising:
   (a) a housing;
   (b) a hollow needle secured near its posterior end to the anterior end of said housing and having an anterior end which is directed laterally;
   (c) a displaceable piston located in said housing, capable of traveling between a fixed forward displaceable piston position and a fixed back displaceable piston position, said piston positions being a preselected distance apart;
   (d) a flexible blind end catheter located in said needle, passing through said displaceable piston, said blind end catheter preventing coring of tissues during the forward travel of said needle and serving to transmit tissue pressure to said displaceable piston;
   (e) a grasping means connected to said displaceable piston for alternately grasping or releasing said catheter;
   (f) means for releasably locking said displaceable piston to said housing at said back displaceable piston position; and
   (g) means for biasing said displaceable piston toward said front piston position.

2. An assembly as in claim 1 wherein said means for releasably locking includes a removable pin capable of penetrating both said housing and said displaceable piston.

3. An assembly as in claim 1 wherein said means for releasably locking said displaceable piston to said housing at said back displaceable piston position is a bayonet safety latch.

4. An assembly as in claim 1 wherein said means for biasing is a spring.

5. An assembly as in claim 1 wherein said spring is in the form of a coil spring.

6. An assembly as in claim 1 wherein said biasing means includes a biasing piston located posteriorly from said displaceable piston.

7. An assembly as in claim 6 wherein said biasing means further includes a compressible fluid hydraulically connecting said displaceable piston and said biasing piston.

8. An assembly as in claim 6 wherein said biasing means further includes a mechanical element mechanically connecting said biasing piston and said displaceable piston.

9. An assembly as in claim 8 wherein said mechanical element is a spring.

10. A device as in claim 1 wherein said grasping means includes a cylindrical member made of a compressible solid surrounding said catheter, said cylindrical member located in a cylindrical cavity, which cavity is located in said displaceable piston.

11. A device as in claim 10 wherein said cylindrical member is capable of being compressed sufficiently to grasp said catheter and prevent said catheter from moving.

12. A device as in claim 1 wherein said grasping means includes two opposing annular members surrounding said catheter, said annular members located in an elliptical cavity, which cavity is located in said displaceable piston.

13. A device as in claim 12 wherein said annular members are capable of being rotated so as to alternately come into sufficiently close proximity of each other so as to grasp said catheter and prevent said catheter from moving, or to separate sufficiently so as to allow said catheter to move freely.

* * * * *